United States Patent [19]

Antelman

[11] Patent Number: 5,676,977
[45] Date of Patent: Oct. 14, 1997

[54] METHOD OF CURING AIDS WITH TETRASILVER TETROXIDE MOLECULAR CRYSTAL DEVICES

[75] Inventor: Marvin S. Antelman, Rehovot, Israel

[73] Assignee: Antelman Technologies Ltd., Providence, R.I.

[21] Appl. No.: 658,955

[22] Filed: May 31, 1996

Related U.S. Application Data

[63] Continuation-in-part of Ser. No. 310,859, Sep. 22, 1994, abandoned.

[51] Int. Cl.$^6$ ................................................. A61K 33/38
[52] U.S. Cl. ................................... 424/618; 514/495
[58] Field of Search ............................ 424/618; 514/495

[56] References Cited

U.S. PATENT DOCUMENTS

| | | | |
|---|---|---|---|
| 4,415,565 | 11/1983 | Wysor | 424/618 |
| 4,915,955 | 4/1990 | Gömöri | 424/616 |
| 4,952,411 | 8/1990 | Fox, Jr. et al. | 424/618 |
| 5,073,382 | 12/1991 | Antelman | 424/604 |
| 5,078,902 | 1/1992 | Antelman | 424/618 |
| 5,089,275 | 2/1992 | Antelman | 424/602 |
| 5,211,855 | 5/1993 | Antelman | 424/618 |
| 5,223,149 | 6/1993 | Antelman | 424/618 |
| 5,336,499 | 8/1994 | Antelman | 424/405 |
| 5,571,520 | 11/1996 | Antelman | 424/618 |

OTHER PUBLICATIONS

"Is The AIDS Virus A Science Fiction?" by Peter H. Duesberg and Bryan J. Ellison, *Policy Review*, Summer 1990, pp. 40–51.

*Primary Examiner*—Amy Hulina
*Attorney, Agent, or Firm*—Salter & Michaelson

[57] ABSTRACT

The diamagnetic semiconducting molecular crystal tetrasilver tetroxide ($Ag_4O_4$) is utilized for destroying the AIDS virus, destroying AIDS synergistic pathogens and immunity suppressing moieties (ISM) in humans.

A single intravenous injection of the devices is all that is required for efficacy at levels of about 40 PPM of human blood. The device molecular crystal contains two mono and two trivalent silver ions capable of "firing" electrons capable of electrocuting the AIDS virus, pathogens and ISM. When administered into the bloodstream, the device electrons will be triggered by pathogens, a proliferating virus and ISM, and when fired will simultaneously trigger a redox chelation mechanism resulting in divalent silver moieties which chelate and bind active sites of the entities destroying them. The devices are completely non-toxic. However, they put stress on the liver causing hepatomegaly, but there is no loss of liver function.

3 Claims, No Drawings

METHOD OF CURING AIDS WITH TETRASILVER TETROXIDE MOLECULAR CRYSTAL DEVICES

This application is a continuation-in-part of patent application Ser. No. 08/310,859 filed Sep. 22, 1994, now abandoned.

BACKGROUND OF THE INVENTION

The present invention relates to the employment of molecular crystals as anti-AIDS devices, but more particularly to the molecular crystal semiconductor tetrasilver tetroxide $Ag_4O_4$ which has two monovalent and two trivalent silver ions per molecule, and which through this structural configuration enables intermolecular electron transfer capable of killing viruses and binding them to the resulting silver entity so that a single intravenous injection will completely obliterate acquired immune deficiency syndrome (AIDS) in humans. Furthermore, said devices are capable of killing pathogens and purging the bloodstream of immune suppressing moieties (ISM) whether or not created by the AIDS virus (HIV); so as to restore the immune system.

The present invention is based on concepts previously elucidated in applicant's U.S. Pat. No. 5,336,499 which discloses the destruction and inhibition of bacteria, algae and the AIDS virus in nutrient life supporting systems by using said silver oxide devices. Example 3 of said patent discloses that 18 PPM of said crystal devices could totally suppress the AIDS virus (page 6, line 5). Subsequent to the filing of the aforementioned patent, further testing revealed complete 100% destruction of the AIDS virus in vitro at 20 PPM, and the fact that said devices were harmless when ingested and inhaled, being non-toxic.

Encouraged by these evaluations and successes, applicant obtained permission to evaluate the crystals in vitro against murine acquired immune deficiency syndrome (MAIDS). Only one facility in the State of Israel is licensed for these evaluations, namely, the Kaplan Hospital in Rehovot, Israel, which is affiliated with the Hebrew University-Hadassah Medical School where said evaluations were done.

The initial evaluations entailed experimenting with various silver moieties cited in applicant's aforementioned patent, concentrations, non-reactive buffers and modes of administration. After about 18 months of judicious efforts and initial failures, success was finally achieved in destroying the MAIDS virus in C57BL mice with a single intravenous injection. The results of this test program comprise Example 5 of U.S. Pat. No. 5,336,499. After success with mice, the inventor was able to test the efficacy of said devices on two select etiological groups of terminal AIDS patients in a clinic in Tegucigalpa, Honduras, Central America.

The AIDS patients comprised the etiological subgroups, Candidiasis and Wasting Syndrome. Current indicator diseases for diagnosing AIDS which have been expanded by the CDC, fall into the following five major categories with the approximate percent distribution among AIDS patients:

| | | |
|---|---|---|
| 1. P. carinii pneumonia | 51% | |
| 2. Wasting syndrome | 19% | |
| 3. Candidiasis | 13% | |
| 4. Kaposi's sarcoma | 11% | |
| 5. Dementia | 6% | |

This invention concerns itself with the treatment and cure of candidiasis and wasting syndrome AIDS patients with Tetrasil\*. These two groups account for approximately one third of AIDS cases.

\*Trademark of Holipharm Corporation (of Israel) for $Ag_4O_4$

Stedman's Medical Dictionary (Williams & Wilken's 26th Ed., 1995) defines wasting syndrome "as a condition of 10% weight loss in conjunction with diarrhea or fever . . . Associated with AIDS (p. 1744)."

OBJECTS OF THE INVENTION

The main object of the invention is to provide for a molecular scale device of a single tetrasilver tetroxide crystalline molecule capable of restoring the immunity of AIDS afflicted humans of the two AIDS etiological subgroups, candidiasis and wasting syndrome.

Another object of the invention is to provide for immunity restoration in said AIDS afflicted humans through a single injection.

Another object of this invention is to destroy ISM in humans manifesting AIDS diseases of said AIDS etiological subgroups irrespective as to whether said ISM was HIV induced, since it is known that humans may manifest AIDS and still be HIV negative, and thus restore the immune system in said humans.

Another object of this invention is to destroy the AIDS virus when present in the systems of said AIDS afflicted humans.

SUMMARY OF THE INVENTION

This invention relates to a molecular scale device not only capable of destroying the AIDS virus, but of purging the human bloodstream of pathogens and restoring immunity to AIDS patients of the candidiasis and wasting syndrome categories. Said molecular device consists of a single crystal of tetrasilver tetroxide ($Ag_4O_4$). The crystal lattice of this molecule has a unique structure since it is a diamagnetic semiconducting crystal containing two mono and two trivalent silver ions, which in effect are capable of "firing" electrons under certain conditions which will destroy AIDS viruses, other pathogens and immune suppressing moieties (ISM), not only through the electrocution mode, but also by a binding process which occurs simultaneously with electron firing, namely, binding and chelation of divalent silver, i.e., the resulting product of the electron transfer redox that occur when the monovalent silver ions are oxidized and the trivalent ions are reduced in the crystal. The binding/chelation effect occurs at active sites of the AIDS virus, pathogens and ISM. Because of the extremely minute size of a single molecule of this crystal, several million of these devices may be employed in concert to destroy a virus colony to purge a life support system of ISM and pathogens with the consumption of only parts per trillion of the crystal devices. Thus an optimum of 40 PPM of the devices by weight of human blood was found to be sufficient to completely obliterate AIDS. This concentration is slightly over double of the optimum concentration recommended in applicant's aforementioned U.S. patent for the destruction of the human AIDS virus in vitro. Other details concerning the structure of the crystal and its mechanism against pathogens, the AIDS virus and ISM would analogously hold here, and have already been further elucidated in said patent.

The actual destruction of pathogens, ISM and the AIDS virus is effectuated by injection of a suspension of these devices in distilled or deionized water with a non-reacting electrolyte directly, i.e. intravenously, into the bloodstream. A single injection is all that is required under these conditions. Accordingly, humans injected in this manner, upon being inspected after three weeks or more had elapsed and compared with similar humans that had been given placebos, were completely cured of AIDS. The control group still manifested AIDS. Accordingly, the tetrasilver tetroxide device performed in concert with and in full conformity with the ultimate objects of this invention. Furthermore, three out of four wasting syndrome terminal patients and four out of the five candidiasis terminal patients were still alive in 1995 after a year and a half had elapsed from their initial injection. By that time all the AIDS patients had been released from the clinic and allowed to return home.

Other objects and features of the present invention shall become apparent to those skilled in the art when the present invention is considered in view of the accompanying examples. It should, of course, be recognized that the accompanying examples illustrate preferred embodiments of the present invention and are not intended as a means of defining the limits and scope of the present invention.

EXAMPLE 1

Five patients afflicted with AIDS of the candidiasis etiological category were segregated for Tetrasil treatment. The rationale for selecting them was based on facts presented in an article by Peter H. Duesberg and Brian J. Ellison entitled "Is The AIDS Virus A Science Fiction?" (*Policy Review*, Summer 1990 pp. 40–51). Only the factual presentations of the article were utilized and the hypothesis of the authors was ignored. The facts presented in the article related to the method of selecting AIDS patients based on the five aforementioned etiological subgroups targeted by the CDC, and the evidence presented, that there is AIDS without HIV as well as with it so that an anti-viral agent in most instances will not necessarily restore the immunity system.

Evaluations with Tetrasil were conducted on AIDS patients at Lucha Contra el Sida, Comayaguela, Honduras. The patients two weeks prior to inoculation were removed from their AZT, AIDS therapy. Tetrasil was administered at approximately 40 PPM of blood volume per patient as a suspension in a proprietary buffer solution (pH=6.5), supplied by Holipharm Corporation.

The results of evaluations with candidiasis are tabulated in Table I under its disease category. All patients evaluated were terminal. Some, however, were in moderate (m) condition and others in poor (p) as designated in the Table. The I and F designations refer to initial and final values as shown. WBC indicates white cell blood count. The H column, following CD 8, indicates whether hepatomegaly occurred.

This was an unfortunate consequence of the treatment which resulted in enlarged livers in all patients except the second one. Despite hepatomegaly, there was no interference with liver function.

The onset of hepatomegaly was not spontaneous and varied from patient to patient, being in the range of 4–16 days.

It should also be noted that shortly after injection of Tetrasil there were indications of fever (symbolized by T in the $Ag_4O_4$ column), sometimes accompanied by fatigue (F). The body temperature was invariably 38.5° C. (101.3° F.). This was indicative of restoration of the immune response of the body, since normally the body will destroy pathogens when the immune system is functional by raising the temperature. The patient who died; first responded favorably to Diflucan, which previously gave no response. He was cured of his candidiasis, but unfortunately succumbed to his previous body damage. All the other candidiasis syndrome people who previously did not respond to the indicated medications subsequently responded after the Tetrasil treatment. Further evidence of the recovery of the AIDS patients manifested itself 30 days after the initial injection when white blood cell counts were taken. They are shown in Table I under the WBC column, which gives the initial and final WBC. All candidiasis patients showed a dramatic increase in their white blood cell counts, indicative of the restoration of their immunity systems.

EXAMPLE 2

The above protocol of Example 1 was repeated with AIDS patients exhibiting wasting syndrome. The results of their treatment are tabulated in Table I under the disease category of said syndrome. It should be noted that two of the four wasting syndrome patients showed improved white blood counts. The female patient, whose condition improved from poor and terminal to be among the living, showed a decrease in the WBC. However, she showed an increase in body temperature which was indicative of immune response. The test results indicate that one cannot rely on a single factor to indicate the demise of AIDS. The usual HIV marker CD 4 initial and final are irrelevant. ISM suppression appears to be more critical than the destruction of HIV. AIDS was suppressed, any permanent damage that had been done to the patients in the course of their succumbing to AIDS was not obviously cured or corrected by said crystal device treatment, rather said injury persisted and the patient was improved with respect to AIDS but still suffered from said permanent injury or impairment previously inflicted.

TABLE I

Response of AIDS Patients to Single 40 PPM $Ag_4O_4$ Inoculation

| DISEASE Group | PATIENT | | | Date Inoc. 1994 | WBC | | CD 4 | | CD 8 | H | DEATH 1944 | Weight Lbs. | | $Ag_4O_4$ |
|---|---|---|---|---|---|---|---|---|---|---|---|---|---|---|
| | Sex | Age | Medictn | | I | F | I | F | | | | I | F | |
| Candidiasis | M p | 28 | Diflucan | 5/5 | 1,200 | 4,200 | 41 | — | 221 | + | 6/11 | 82 | 76 | T |
| | F m | 33 | " | 5/5 | 6,000 | 6,700 | 554 | 872 | 394 | — | | 98 | 98 | T |
| | F m | 33 | Ketaconzl | 5/27 | 2,600 | 3,850 | 248 | 181 | 951 | + | | 123 | 123 | T |
| | M p | 62 | " | 6/2 | 3,300 | 3,700 | 89 | 237 | 59 | + | | 105 | 92 | F |
| | F m | 31 | Pentamidn | 6/2 | 2,400 | 3,050 | 9 | 181 | 65 | + | | 121 | 118 | Pain |
| Wasting | M m | 27 | | 5/27 | 3,600 | 4,600 | 39 | 14 | 709 | + | | 119 | 120 | T |
| Syndrome | M m | 28 | | 5/27 | 2,750 | — | 10 | — | 60 | + | 7/19 | 121 | 119 | T, F |
| | F p | 43 | | 5/27 | 3,600 | 2,700 | 68 | 246 | 248 | + | | 101 | 98 | T, F |
| | M m | 19 | | 5/10 | 3,850 | 5,400 | 137 | 36 | 48 | + | | 103 | 106 | T, F |

As this invention may be embodied in several forms without departing from the spirit or essential characteristics thereof, the present embodiments are therefore illustrative and not restrictive, since the scope of the invention is defined by the appended claims rather than by the description preceding them, and all changes that fall within the metes and bounds of the claims or that form their functional as well as conjointly cooperative equivalents, are therefore intended to be embraced by these claims.

What is claimed is:

1. A method of treating AIDS-afflicted humans comprising injecting a multitude of tetrasilver tetroxide molecular crystals into the bloodstream of the human subject.

2. A method for increasing white blood cell counts in AIDS-afflicted humans comprising injecting a multitude of tetrasilver tetroxide molecular crystals into the bloodstream of the human subject.

3. Methods of treating AIDS-afflicted humans according to claims 1-2 where the concentration of said molecular crystals is approximately 40 PPM of the total blood weight of the human subject.

* * * * *